United States Patent
Palko et al.

(10) Patent No.: US 11,027,095 B2
(45) Date of Patent: Jun. 8, 2021

(54) ARCHFLO MIDLINE CATHETER

(71) Applicant: MEDICAL COMPONENTS INC., Harleysville, PA (US)

(72) Inventors: Michael Palko, Perkasie, PA (US); Michael Anstett, New Port Richey, FL (US); Rose Rowan, Mantua, NJ (US); John Timko, Rochester Hills, MI (US)

(73) Assignee: MEDICAL COMPONENTS INC., Harleysville, PA (US)

( * ) Notice: Subject to any disclaimer, the term of this patent is extended or adjusted under 35 U.S.C. 154(b) by 231 days.

(21) Appl. No.: 15/836,054

(22) Filed: Dec. 8, 2017

(65) Prior Publication Data

US 2018/0169382 A1 Jun. 21, 2018

Related U.S. Application Data

(60) Provisional application No. 62/435,887, filed on Dec. 19, 2016.

(51) Int. Cl.
*A61M 25/00* (2006.01)

(52) U.S. Cl.
CPC .... *A61M 25/0068* (2013.01); *A61M 25/0097* (2013.01); *A61M 2025/0008* (2013.01); *A61M 2025/0073* (2013.01); *A61M 2205/583* (2013.01); *A61M 2205/584* (2013.01)

(58) Field of Classification Search
CPC .......... A61M 25/0068; A61M 25/0067; A61M 25/007; A61M 25/0097; A61M 2205/584; A61M 2205/583; A61M 2025/0073; A61M 2025/0008
See application file for complete search history.

(56) References Cited

U.S. PATENT DOCUMENTS

| | | | |
|---|---|---|---|
| 8,603,067 B2 | 12/2013 | Lareau et al. | |
| 9,468,496 B2 | 10/2016 | Goshayeshgar et al. | |
| 2004/0193102 A1* | 9/2004 | Haggstrom | A61M 25/0068 604/43 |
| 2005/0080398 A1* | 4/2005 | Markel | A61M 1/3661 604/508 |
| 2009/0306539 A1* | 12/2009 | Woodruff | A61B 5/205 600/561 |
| 2011/0172642 A1* | 7/2011 | Lareau | A61M 25/0017 604/523 |
| 2011/0196190 A1* | 8/2011 | Farnan | A61M 1/3659 600/16 |
| 2012/0016345 A1* | 1/2012 | Carter | A61M 39/10 604/533 |

(Continued)

OTHER PUBLICATIONS

International Search Report and Written Opinion dated Mar. 9, 2018 issued in PCT Patent Application No. PCT/US2017/065259.

*Primary Examiner* — Amber R Stiles
(74) *Attorney, Agent, or Firm* — Fisherbroyles LLP; Keats A. Quinalty

(57) ABSTRACT

A midline catheter is provided. The midline catheter includes a shaft defining a lumen, the shaft having a distal end and a proximal end. The distal end includes two or more opposing notches thereon, each of the notches having an open notch distal end and an opposing notch proximal end formed as an arch. The catheter may also include written indicia thereon to indicate that it is a midline catheter and/or is power injectable or non-power-injectable.

19 Claims, 4 Drawing Sheets

(56) References Cited

U.S. PATENT DOCUMENTS

2013/0046224 A1\* 2/2013 Ravenscroft ...... A61M 25/0194
       604/5.01
2013/0158488 A1   6/2013 Weaver et al.
2013/0267912 A1\* 10/2013 Cox ................. A61M 25/0009
       604/256

\* cited by examiner

ARCHFLO MIDLINE CATHETER

RELATED APPLICATIONS

This application claims the benefit of priority to U.S. Provisional Application Ser. No. 62/435,887 filed on Dec. 19, 2016, the entirety of which is hereby incorporated by reference.

FIELD OF THE INVENTION

This invention relates generally to vascular access and more particularly to midline catheters.

BACKGROUND OF THE INVENTION

Peripheral intravenous catheters (PIV) typically remain in place or "dwell" from a few hours to four days. For longer therapies, PIVs are serially replaced or an extended use (extended dwell) IV catheter is inserted. The most popular extended dwell IV catheter is the peripherally inserted central catheter (PICC). The end or tip or the catheter is generally positioned in the lower one-third of the cavo-atrial junction. PICC insertions require a highly skilled nurse or physician for insertion as they may employ a variety of special components including a complicated, large-gauge, peel-away introducer and/or fine-gauge wires that are inserted into the vein.

Multiple complications can arise from the placement of a PICC line ranging from simple bruising to significant tissue damage. In all cases, a post-procedural chest X-Ray is used to indicate whether or not the catheter is appropriately positioned in the superior vena cava. Sometimes, the catheter tip is found to reside either in the jugular vein, in the right atrium of the heart, or malpositioned elsewhere. In the event of improper catheter tip placement, the PICC must be manipulated into proper position, removed or pulled back into a sub-optimal, non-central position. Repositioning of a PICC line can be both difficult and costly, as it often requires the use of a Fluoroscope for X-Ray imaging guidance. Failure to reposition a poorly placed catheter tip can result in complications such as abnormal heart rhythms, vessel damage, or, rarely, a perforation of the superior vena cava or other central vessels. Many physicians are hesitant to order a PICC line for these same reasons.

In between the PIV and PICC is a mid-length (midline) catheter which is designed for a moderate extended dwell period of between six and thirty days. Midline catheters are peripheral infusion devices inserted via the antecubital fossa with the tips terminating in either the basilic, cephalic, or brachial vein, distal to the shoulder, at or below the axillary line. Most technicians consider the basilic vein to be optimal due to the diameter of the vein.

As midline catheters are intended for extended use (e.g. up to 30 days), maintaining patency of the catheter is a concern. Therefore, what is needed is a midline catheter that has enhanced patency that will increase dwell time by minimizing events that may lead to catheter occlusion due to blood clots and/or suctioning to the vessel wall.

BRIEF SUMMARY OF THE INVENTION

The foregoing needs are addressed by the midline catheter in accordance with the invention.

In one aspect of the invention a catheter with enhanced patency is provided. This is accomplished by shortening the lumen from 20 cm (as in a standard midline catheter) to 10 cm to reduce the mechanical vessel irritation from shoulder movement.

In another aspect of the invention the catheter includes a distal end that includes a radiused edge, which reduces the mechanical vessel irritation during insertion from shoulder movement during dwell. Unlike conventional midline catheters the midline catheter in accordance with the invention includes a non-trimmable distal tip.

In another aspect of the invention the distal end of the catheter includes opposing notches at the distal end that reduces the likelihood of catheter occlusion due to blood clots or suctioning to the vessel wall.

In another aspect of the invention the notches include an arched portion positioned on and cut into the shaft of the catheter.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION OF THE INVENTION

Figure 1:
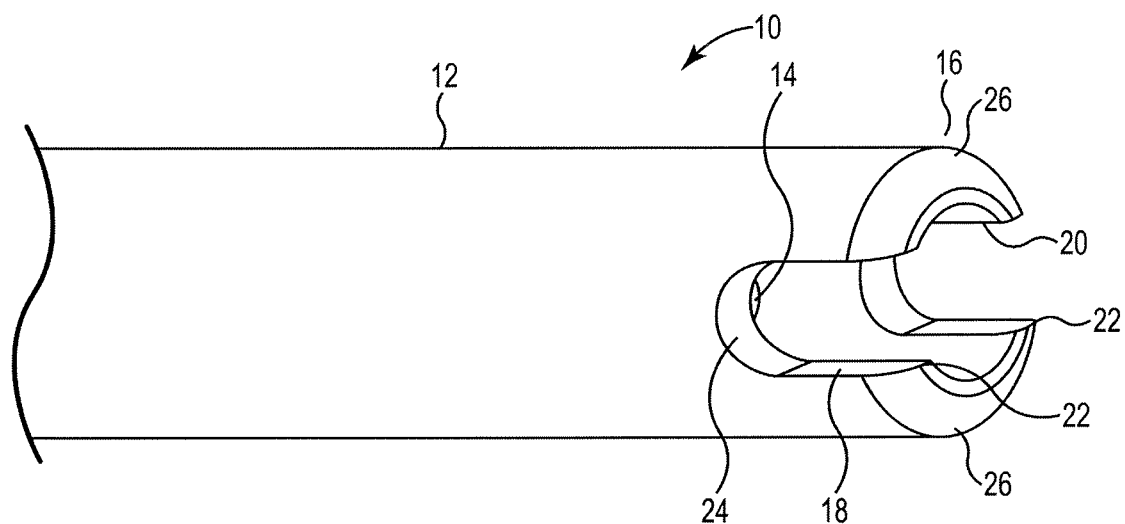
FIG. 1 is a perspective view of the midline catheter in accordance with the invention showing the distal tip.
Figure 2:
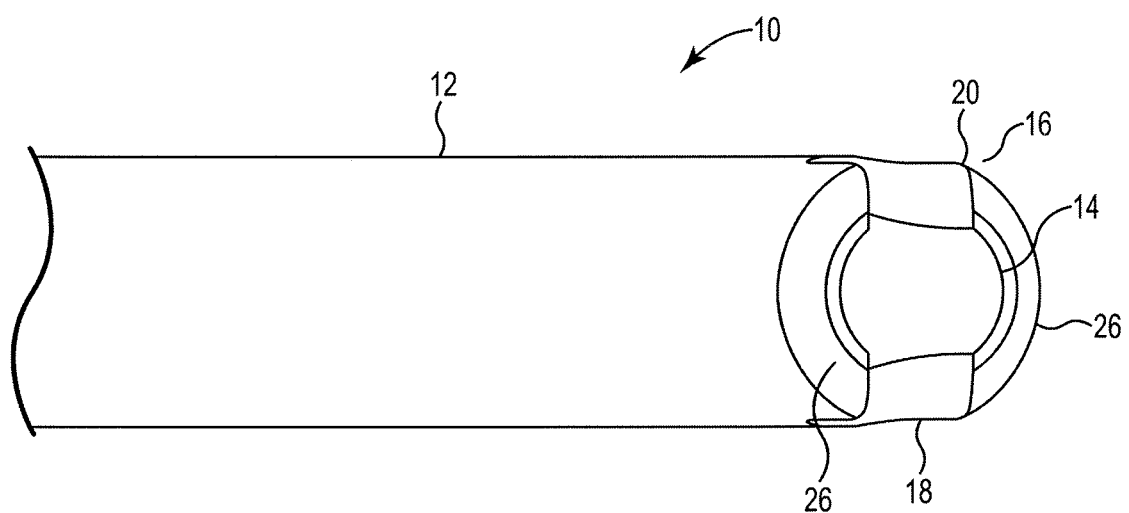
FIG. 2 is a perspective view of the midline catheter in accordance with the invention showing the distal tip.
Figure 3:
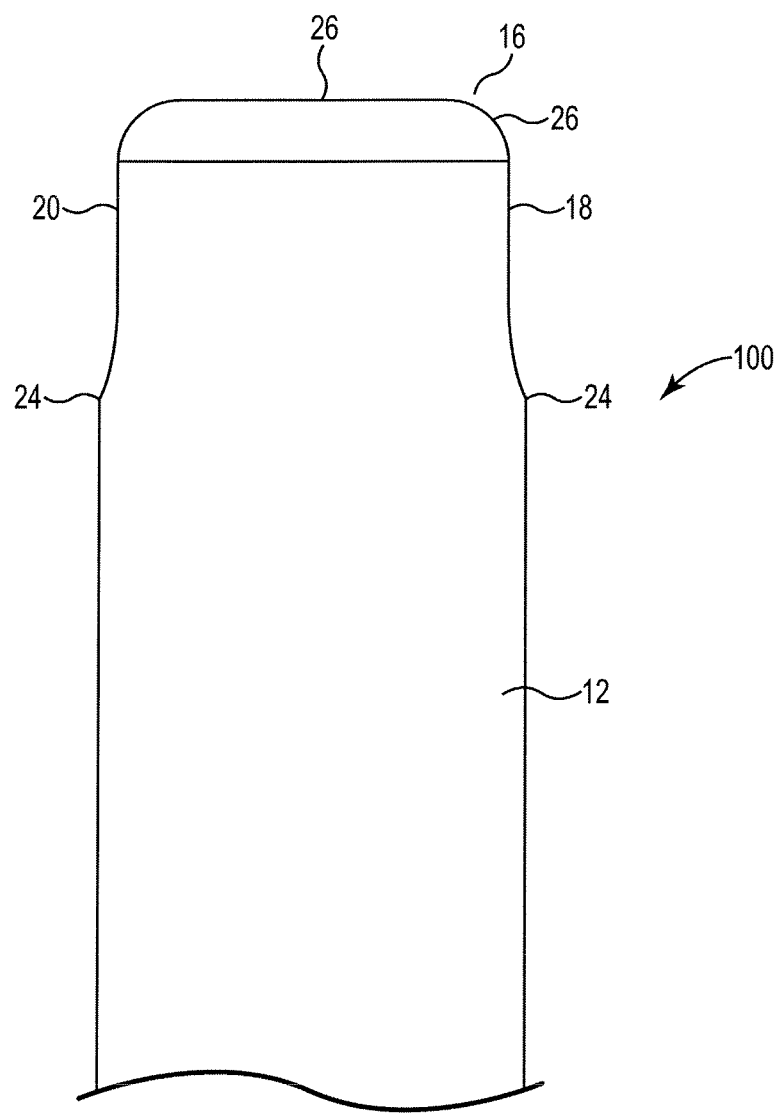
FIG. 3 is a perspective side view of the midline catheter in accordance with the invention showing the radiused edge of distal tip and the arched notch.
Figure 4:
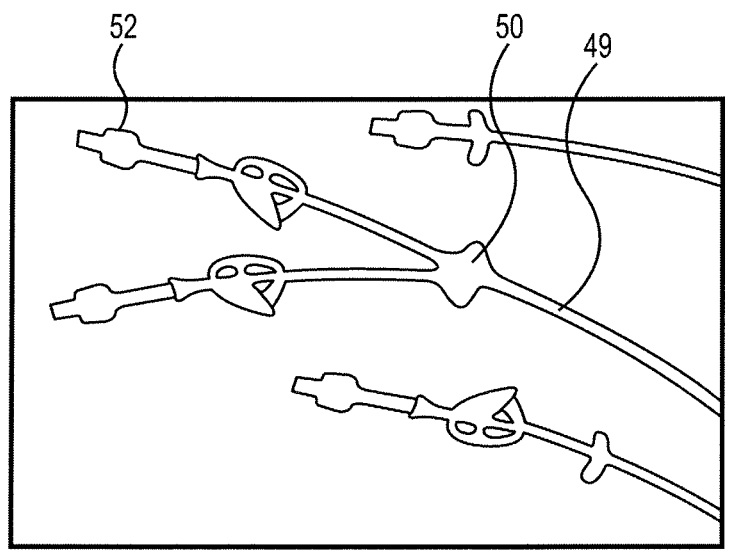
FIG. 4 is a perspective view depicting a hub and luer of a catheter.

The midline catheter in accordance with the invention advantageously reduces mural thrombus formation along with a higher potential of extended utility for blood return. Referring now to FIGS. 1-3, the midline catheter 10 in accordance with the invention includes catheter shaft 12, catheter lumen 14 and distal tip 16. Proximal end 49 is operably coupled to a luer 52, extension, clamp, ID tag and hub 50.

Distal tip 16 includes a pair of opposing notches 18, 20 thereon. Notches 18, 20 each include a distal end 22 and a proximal end 24. Proximal end 24 is formed as an arch in the sidewall of catheter shaft 12. The arch shape is advantageous in that it eliminates corners that might encourage clots to form. Notches 18, 20 enhances the patency of catheter 10 by preventing occlusion of lumen 14. Notches 18, 20 increase the open, patent area of the catheter allowing for partial occlusion while still remaining patent. Those of skill in the art will appreciate that more than two opposing notches may be positioned at the distal tip of the catheter depending on the size of the catheter and depending on the dimensions of the notch. The dimensions of each of the opposing arches are approximately 0.020 inches to 0.025 inches wide and 0.038 inches by 0.042 inches in length. Preferably the dimensions are 0.022 inches wide and 0.040 inches in length. Those of skill in the art will also appreciate that the dimensions of the notches 18, 20 may vary according to need and size of the catheter.

In addition, the distal end 22 of midline catheter 10 in accordance with the invention advantageously includes a radius 26 circumferentially disposed on the distal end 22 for reducing mechanical irritation during insertion and dwell periods. The radius may be from 0.007 inches to 0.010 inches and preferably 0.008 inches.

The midline catheter 10 in accordance with the invention may include a 3F single, 4F single and 4F double sized catheter. The catheter may have a length of approximately 10 cm to prevent the catheter from reaching the shoulder region which in turn reduces mechanical vessel irritation from shoulder movement.

After implantation it is difficult to determine whether a catheter is a PICC or a midline without referring to documentation regarding the implantation procedure. Therefore, it is anticipated that the hub 50 and luer 52 may include printed indicia thereon to clearly identify it as a "midline" catheter and/or whether or not the catheter is "power injectable." Such indicia may include a symbol, words and may additionally include a color such as yellow, red, green, etc. Those of skill in the art will appreciate that the printed indicia may also be printed on the catheter shaft.

Those of skill in the art will also appreciate that the catheter 10 may be power injectable or may be inserted manually.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application. Thus, the breadth and scope of the present invention should not be limited by any of the above described embodiments. Rather, the scope of the invention should be defined in accordance with the following claims and their equivalents.

What is claimed:

1. A midline catheter comprising:
   a shaft defining a lumen, said shaft having a distal end and a proximal end wherein said distal end includes two or more opposing notches thereon, each of said notches having an open notch distal end and an opposing notch proximal end formed as an arch;
   wherein an interior of the shaft is undivided between the proximal end of the shaft and the proximal end of each of the two or more opposing notches;
   wherein said distal end includes a radiused edge circumferentially disposed thereon;
   wherein said catheter further includes a luer and a hub coupled to the proximal end and wherein an indicia is printed on the luer, the hub, the shaft, or combinations of the foregoing.

2. The midline catheter of claim 1 wherein each of said arches are formed in the shaft of the midline catheter.

3. The midline catheter of claim 1 wherein the radiused edge is configured to reduce mechanical irritation during an insertion and a dwell period.

4. The midline catheter of claim 1 wherein said catheter is sized as 3F single, 4F single, or 4F double.

5. The midline catheter of claim 1 wherein said printed indicia indicates that the catheter is power-injectable.

6. The midline catheter of claim 1 wherein said printed indicia indicates that the catheter is not power-injectable.

7. The midline catheter of claim 1 wherein said printed indicia indicates that the catheter is a mid-line catheter.

8. The midline catheter of claim 1 wherein a length of the catheter is 10 cm.

9. The midline catheter of claim 1 wherein a dimension of each of said notches is from 0.020 inches to 0.025 inches wide and 0.038 inches by 0.042 inches in length.

10. The midline catheter of claim 9 wherein the dimension of each of said notches is 0.022 inches wide and 0.040 inches in length.

11. The midline catheter of claim 1 wherein a dimension of the radius of the radiused edge is from 0.007 inches to 0.010 inches.

12. The midline catheter of claim 11 wherein the dimension of the radius is 0.008 inches.

13. The midline catheter of claim 1 wherein the interior of the shaft between the proximal end of each of said notches is substantially circular.

14. A midline catheter comprising:
    a shaft defining a lumen, said shaft having a distal end and a proximal end wherein said distal end includes two or more opposing notches thereon, each of said notches having an open notch distal end and an opposing notch proximal end formed as an arch;
    wherein an interior of the shaft is undivided between the proximal end of the shaft and the proximal end of each of the two or more opposing notches;
    wherein said distal end includes a radiused edge circumferentially disposed thereon;
    wherein said catheter further includes a luer and a hub and wherein at least one of the luer, the hub, or the shaft is color coded to indicate that the catheter is power-injectable or non-power-injectable.

15. A midline catheter comprising:
    a shaft defining a lumen, the shaft having a distal end and a proximal end;
    the distal end includes at least two opposing notches, with each notch of the at least two opposing notches having an open notch distal end and an opposing notch proximal end formed as an arch;
    wherein an interior of the shaft between the proximal end of each of the at least two opposing notches is substantially circular;
    wherein the distal end includes a radiused edge circumferentially disposed thereon;
    wherein said catheter further includes a luer and a hub coupled to the proximal end and wherein an indicia is printed on the luer, the hub, the shaft, or combinations of the foregoing.

16. The midline catheter of claim 15 wherein each of the arches are formed in the shaft of the midline catheter.

17. The midline catheter of claim 15 wherein the radiused edge is configured to reduce mechanical irritation during an insertion and a dwell period.

18. The midline catheter of claim 15 wherein the catheter is sized as 3F single, 4F single, or 4F double.

19. The midline catheter of claim 15 wherein the interior of the shaft is undivided between the proximal end and the proximal end of each of said notches.

* * * * *